United States Patent
Fine

(10) Patent No.: US 12,241,893 B2
(45) Date of Patent: *Mar. 4, 2025

(54) BEAD-BASED ANALYSIS OF A SAMPLE

(71) Applicant: Alentic Microscience Inc., Halifax (CA)

(72) Inventor: Alan Marc Fine, Prospect (CA)

(73) Assignee: Alentic Microscience Inc., Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/674,179

(22) Filed: May 24, 2024

(65) Prior Publication Data

US 2024/0385184 A1   Nov. 21, 2024

Related U.S. Application Data

(60) Continuation of application No. 18/200,301, filed on May 22, 2023, now abandoned, which is a division of
(Continued)

(51) Int. Cl.
   *G01N 33/543* (2006.01)
   *G01N 21/41* (2006.01)
   (Continued)

(52) U.S. Cl.
   CPC ....... *G01N 33/54313* (2013.01); *G01N 21/41* (2013.01); *G01N 21/55* (2013.01);
   (Continued)

(58) Field of Classification Search
   CPC ....... G01N 33/54313; G01N 33/56983; G01N 21/41; G01N 21/55; G01N 21/59; G01N 2021/1771
   See application file for complete search history.

(56) References Cited

U.S. PATENT DOCUMENTS

| 9,041,790 B2 | 5/2015 | Fine et al. |
| 9,075,225 B2 | 7/2015 | Fine et al. |

(Continued)

FOREIGN PATENT DOCUMENTS

| CN | 1635988 | 7/2005 |
| CN | 105143886 | 12/2015 |

(Continued)

OTHER PUBLICATIONS

Appleblom et al., "Homogeneous TR-FRET High-Throughput Screening Assay for Calcium-Dependent Multimerization of Sorcin", www.sbsonline.org, Society for Biomolecular Sciences, 2007, 7 pages.

(Continued)

*Primary Examiner* — Gailene Gabel
(74) *Attorney, Agent, or Firm* — Fish & Richardson P.C.

(57) ABSTRACT

A method includes attaching two or more beads to each unit of one or more units of a chemical component in a sample, to form, for each unit of the chemical component, a multi-bead complex including two or more beads and the unit of the chemical component; placing the sample on a surface of an image sensor; at the image sensor, receiving light originating at a light source, the received light including light reflected by, refracted by, or transmitted through the beads of the multi-bead complexes; at the image sensor, capturing one or more images of the sample from the received light; and identifying, in at least one of the images of the sample, separate multi-bead complexes, the identifying of the separate multi-bead complexes including associating the two or more beads of each of the multi-bead complexes based on proximity to one another.

20 Claims, 6 Drawing Sheets

Related U.S. Application Data application No. 17/674,967, filed on Feb. 18, 2022, now Pat. No. 11,733,239, which is a division of application No. 16/845,458, filed on Apr. 10, 2020, now Pat. No. 11,255,850, which is a continuation-in-part of application No. 16/368,707, filed on Mar. 28, 2019, now Pat. No. 10,684,278.

(51) Int. Cl.
G01N 21/55 (2014.01)
G01N 21/59 (2006.01)
G01N 33/569 (2006.01)
G01N 21/17 (2006.01)

(52) U.S. Cl.
CPC ....... G01N 21/59 (2013.01); G01N 33/56983 (2013.01); G01N 2021/1772 (2013.01)

(56) References Cited

U.S. PATENT DOCUMENTS

| | | |
|---|---|---|
| 9,518,920 B2 | 12/2016 | Fine et al. |
| 9,720,217 B2 | 8/2017 | Fine et al. |
| 9,910,254 B2 | 3/2018 | Fine et al. |
| 9,952,417 B2 | 4/2018 | Fine |
| 9,989,750 B2 | 6/2018 | Fine et al. |
| 10,107,997 B2 | 10/2018 | Fine |
| 10,114,203 B2 | 10/2018 | Fine et al. |
| 10,153,317 B1 | 12/2018 | Fine |
| 10,249,669 B1 | 4/2019 | Fine |
| 10,461,112 B1 | 10/2019 | Fine |
| 10,684,278 B1 | 6/2020 | Fine |
| 10,991,744 B2 | 4/2021 | Fine |
| 11,099,181 B2 | 8/2021 | Fine |
| 11,255,850 B2 | 2/2022 | Fine |
| 11,609,233 B2 | 3/2023 | Fine |
| 11,719,700 B2 | 8/2023 | Fine |
| 12,123,868 B2 | 10/2024 | Fine |
| 2006/0216696 A1 | 9/2006 | Goguen |
| 2011/0065209 A1 | 3/2011 | Heil et al. |
| 2013/0157288 A1 | 6/2013 | Kilfeather et al. |
| 2014/0152801 A1 | 6/2014 | Fine et al. |
| 2016/0041200 A1 | 2/2016 | Fine et al. |
| 2016/0187235 A1 | 6/2016 | Fine et al. |
| 2017/0074870 A1 | 3/2017 | Konry et al. |
| 2017/0293133 A1 | 10/2017 | Fine et al. |
| 2018/0284416 A1 | 10/2018 | Fine et al. |
| 2019/0054466 A1 | 2/2019 | Gershtein |
| 2019/0056384 A1 | 2/2019 | Gershtein |
| 2019/0056385 A1 | 2/2019 | Gershtein |
| 2019/0162648 A1 | 5/2019 | Fine |
| 2020/0309772 A1 | 10/2020 | Fine et al. |
| 2020/0309777 A1 | 10/2020 | Fine et al. |
| 2021/0311037 A1 | 10/2021 | Fine |
| 2021/0311038 A1 | 10/2021 | Fine |
| 2022/0082557 A1 | 3/2022 | Fine |
| 2022/0274109 A1 | 9/2022 | Gershtein |
| 2022/0412968 A1 | 12/2022 | Fine |
| 2023/0164299 A1 | 5/2023 | Fine |
| 2023/0184778 A1* | 6/2023 | Fine .................. G01N 33/5302 436/501 |
| 2023/0288407 A1 | 9/2023 | Fine |

FOREIGN PATENT DOCUMENTS

| | | |
|---|---|---|
| CN | 113631912 | 11/2021 |
| JP | 2002544488 | 12/2002 |
| TW | I641371 | 11/2018 |
| TW | I642780 | 12/2018 |
| WO | WO 2000068692 | 11/2000 |
| WO | WO 2011026030 | 3/2011 |
| WO | WO 2011102903 | 8/2011 |
| WO | WO 2012061778 | 5/2012 |
| WO | WO 2013057634 | 4/2013 |
| WO | WO 2020191480 | 10/2020 |
| WO | WO 2021203201 | 10/2021 |

OTHER PUBLICATIONS

Barua et al., "Challenges associated with Penetration of Nanoparticles Across Cell and Tissue Barriers: A Review of Current Status and Future Prospects", Nano Today, Apr. 2014, 9(2):223-243.

Bidinosti et al., "Novel one step immunoassays to Quantify a-Synuclein: Applications for Biomarker Development and High-throughput Screening", Journal of Biological Chemistry 287(40):33691-33705, Sep. 28, 2012, 16 pages.

Chang et al., "Novel Diagnostic and Predictive Biomarkers in Pancreatic Adenocarcinoma", International Journal of Molecular Sciences, Mar. 2017, 14 pages.

Chavda et al., "A Bead Aggregation Assay for Detection of Low-Affinity Protein-Protein Interactions Reveals Interactions between N-Terminal Domains of Inositol 1,4,5-Trisphosphate Receptors", PLOS/One, Mar. 2013, 7 pages.

Extended European Search Report in European Appln. No. 20779367.0, dated May 2, 2022, 11 pages.

Extended European Search Report in European Appln. No. 21784000.8, dated Aug. 28, 2023, 8 pages.

Hashizume et al., "Openings Between Defective Endothelial Cells Explain Tumor Vessel Leakiness", Am. J. Pathol., Apr. 2000, 156(4):1363-1380.

International Preliminary Report on Patentability in International Application No. PCT/CA2021/050466, mailed on Oct. 20, 2022, 8 pages.

International Search Report and Written Opinion in International Application No. PCT/CA2020/050286, dated Jun. 5, 2020, 9 pages.

Kattke et al., "FRET-based Quantum Dot Immunoassay for Rapid and Sensitive Detection of Aspergillus amstelodami" Sensors 2011, 15 pages.

Medintz et al., "Self assembled nanoscale biosensors based on quantum dot FRET donors", Nature Materials, Oct. 2003, 10 pages.

Miller et al., "Significance of Circulating Tumor Cells Detected by the CellSearch System in Patients with Metastatic Breast Colorectal and Prostate Cancer", Journal of Oncology, Dec. 2009, 8 pages.

Moon et al., "Lensless Imaging for Point of Care Testing," Conf. Proc. IEEE Eng. Med. Biol. Soc., Sep. 2009, 6376-6379, 8 pages.

Notice of Allowance in Chinese Application No. 202180034404.0, dated May 20, 2024, 6 pages (with English Translation).

Notice of Allowance in Japanese Application No. 2021557416, dated Feb. 6, 2024, 6 pages (with English Translation).

Office Action in Chinese Patent Application No. 202180034404.0, dated Dec. 28, 2023, 13 pages (with English Translation).

PCT International Preliminary Report on Patentability in International Appln. No. PCT/CA2020/050286, dated Oct. 7, 2021, 6 pages.

PCT International Search Report and Written Opinion in International Appln. No. PCT/CA2021/050466, dated Jul. 27, 2021, 10 pages.

Shao et al., "Diagnostic Technologies for Circulating Tumour Cells and Exosomes", Bioscience Reports, Feb. 2016, 36(1):E00292.

Shi et al., "Nanoparticles based fluorescence energy transfer (FRET) for biosensing applications", Journal of Materials Chemistry B, Royal Society of Chemistry, 2015, 17 pages.

Tagit et al., "Fluorescence Sensing of Circulating Diagnostic Biomarkers Using Molecular Probes and Nanoparticles", ACS Sensors, Oct. 25, 2017, 16 pages.

Taiwanese Office Action in TW Appln. No. 109110649, dated Mar. 5, 2021, 19 pages with English translation.

Verma et al., "Covalent Immobilization of Doxorubicin in Glycine Functionalized Hydroxyapatite Nanoparticles for pH-Responsive Release", New Journal of Chemistry, 2018, Abstract Only.

Wikipedia.org [online], "Immunoassay", published on May 17, 2021, retrieved on Jun. 14, 2021, retrieved from URL<https://en.wikipedia.org/wiki/Immunoassay>, 7 pages.

(56) References Cited

OTHER PUBLICATIONS

Zeng et al., "Constructions of Silver Triangular Nanoplates-Quantum Dots FRET Systems", Scientific Reports, www.nature.com/scientificreports, May 20, 2016, 8 pages.

Zorko et al., "Cell Penetrating Peptides: Mechanism and Kinetics of Cargo Delivery", Adv. Drug Deliv. Rev. Mar. 2005, 57:529-545.

Communication pursuant to Article 94(3) EPC in European Application No. 20799367.0, mailed on Oct. 9, 2024, 14 pages.

* cited by examiner

BEAD-BASED ANALYSIS OF A SAMPLE

PRIORITY CLAIMS

This application is a continuation of U.S. patent application Ser. No. 18/200,301, filed on May 22, 2023, which is a divisional of U.S. patent application Ser. No. 17/674,967, filed on Feb. 18, 2022 (U.S. Pat. No. 11,733,239, which issued on Aug. 22, 2023), which is a divisional of U.S. patent application Ser. No. 16/845,458, filed on Apr. 10, 2020 (U.S. Pat. No. 11,255,850, which issued on Feb. 22, 2022), which is a continuation-in-part of U.S. patent application Ser. No. 16/368,707, filed on Mar. 28, 2019 (U.S. Pat. No. 10,684,278, which issued on Jun. 16, 2020), the entire contents of each of which are incorporated here by reference.

BACKGROUND

This description relates to bead-based analysis of a sample.

To obtain all the useful information in a sample of whole blood of a patient for purposes of diagnosis, for example, requires not only a complete blood count (CBC) of the various types of blood cells in the blood sample and their hemoglobin content but also a chemical analysis of other components in the acellular portion of blood (e.g., the plasma). Such other components can include molecules and ions of various kinds.

Traditionally, both a CBC and a chemical analysis of blood are performed in a lab on large expensive machines using tubes of venous blood obtained by phlebotomy. Hours or days may be required for the chemical analysis to be completed and the results returned.

SUMMARY

In general, an aspect of the disclosure is a method including attaching two or more beads to each unit of one or more units of a chemical component in a sample, to form, for each unit of the chemical component, a multi-bead complex including two or more beads and the unit of the chemical component; placing the sample on a surface of an image sensor; at the image sensor, receiving light originating at a light source, the received light including light reflected by, refracted by, or transmitted through the beads of the multi-bead complexes; at the image sensor, capturing one or more images of the sample from the received light; and identifying, in at least one of the images of the sample, separate multi-bead complexes, the identifying of the separate multi-bead complexes including associating the two or more beads of each of the multi-bead complexes based on proximity to one another.

Implementations may include one or a combination of two or more of the following features. The method includes identifying a presence of the chemical component based on the identification of the separate multi-bead complexes. The method includes identifying a level of the chemical component based on the identification of the separate multi-bead complexes. Identifying the separate multi-bead complexes includes enumerating the separate multi-bead complexes.

In some implementations, attaching two or more beads to each unit of the chemical component includes binding two or more attachment units to each unit of the one or more units of the chemical component, each of the attachment units also being attached to one or more beads, such that each multi-bead complex includes two or more beads, two or more attachment units, and the unit of the chemical component. In some implementations, the attachment units include antibodies. In some implementations, the attachment units include capsid proteins or other antigens from a pathogen, and the units of the chemical component include antibodies to the pathogen. In some implementations, the pathogen includes a virus. In some implementations, at least two of the two or more attachment units are different from one another. In some implementations, the two or more attachment units bind at different locations of a unit of the chemical component.

Implementations may include one or a combination of two or more of the following features. At least two of the two or more beads of a multi-bead complex have the same reflective, refractive, and transmissive characteristics. At least two of the two or more beads of a multi-bead complex have different reflective, refractive, or transmissive characteristics or combinations of them for the light originating at the light source. The different reflective, refractive, or transmissive characteristics include at least one of colors of the beads, sizes of the beads, shapes of the beads, and birefringence of the beads. Each unit of the chemical component includes an antibody of a pathogenic virus. Placing the sample on the surface of the image sensor includes forming a monolayer of the sample on the surface. Placing the sample on the surface of the image sensor includes confining the sample between the surface of the image sensor and a second surface opposite the surface of the image sensor. The method includes identifying, in at least one of the images of the sample, separate individual beads based on light reflected by, refracted by, or transmitted by each of the separate individual beads, and based on a proximity of each of the separate individual beads to other beads.

In general, an aspect of the disclosure is an apparatus including an image sensor having an array of light sensitive elements at a surface of the image sensor, and one or more computing processors communicatively coupled to the image sensor, the one or more computing processors configured to perform operations including: receiving, from the image sensor, data representative of one or more images of a sample situated at the surface of the image sensor, the sample including one or more multi-bead complexes, each multi-bead complex including two or more beads attached to a unit of a chemical component, in which the one or more images are based on light originating at a light source and received at the image sensor, the received light including light reflected by, refracted by, or transmitted through the beads of the multi-bead complexes; and identifying, in at least one of the images of the sample, separate multi-bead complexes, the identifying of the separate multi-bead complexes including associating the two or more beads of each of the multi-bead complexes based on close proximity to one another.

Implementations may include one or a combination of two or more of the following. The operations include identifying a presence of the chemical component based on the identification of the separate multi-bead complexes. The operations include identifying a level of the chemical component based on the identification of the separate multi-bead complexes. Identifying the separate multi-bead complexes includes enumerating the separate multi-bead complexes.

In some implementations, each multi-bead complex includes two or more attachment units bound to a unit of the chemical component, each of the attachment units also being attached to one or more beads, such that each multi-bead complex includes two or more beads, two or more attachment units, and the unit of the chemical component. In some implementations, the attachment units include antibodies. In some implementations, the attachment units include capsid proteins or other antigens from a pathogen, and the units of the chemical component include antibodies to the pathogen. In some implementations, the pathogen includes a virus. In some implementations, at least two of the two or more attachment units are different from one another. In some implementations, the two or more attachment units bind at different locations of a unit of the chemical component.

Implementations may include one or a combination of two or more of the following. At least two of the two or more beads of a multi-bead complex have the same reflective, refractive, and transmissive characteristics, and the one or more processors are configured to detect the reflective, refractive, and transmissive characteristics. At least two of the two or more beads of a multi-bead complex have different reflective, refractive, or transmissive characteristics or combinations of them for the light originating at the light source, and the one or more processors are configured to detect the reflective refractive, and transmissive characteristics. The different reflective, refractive, or transmissive characteristics include at least one of colors of the beads, sizes of the beads, shapes of the beads, and birefringence of the beads. Each unit of the chemical component includes an antibody of a pathogenic virus. The apparatus includes a second surface opposite the surface of the image sensor, the second surface configured to confine the sample between the second surface and the surface of the image sensor. The second surface is configured to form a monolayer of the sample between the second surface and the surface of the image sensor. The apparatus includes a light source. The operations include enumerating, in at least one of the images of the sample, separate individual beads based on light reflected by, refracted by, or transmitted by each of the separate individual beads, and based on a proximity of each of the separate individual beads to other beads.

These and other aspects, features, implementations, and advantages (1) can be expressed as methods, apparatus, systems, components, program products, business methods, means or steps for performing functions, and in other ways, and (2) will become apparent from the following description and from the claims.

DETAILED DESCRIPTION

Figure 1:
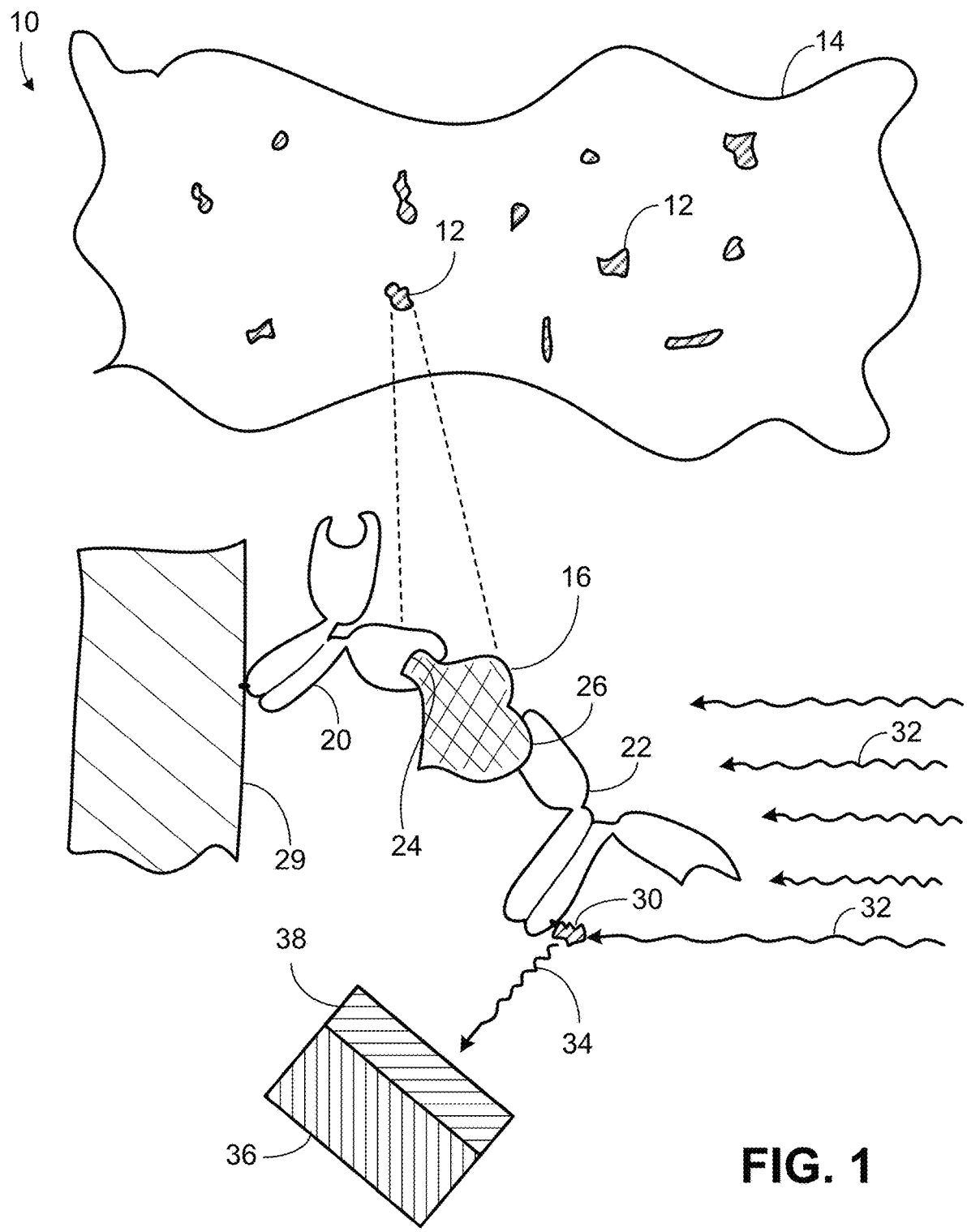
FIG. 1 is a schematic view of an example fluorescence immunoassay technique.

Here we describe a sample analysis technology that in some implementations can perform a chemical analysis of a sample of whole blood alone or in combination with a CBC directly at a point of care within a few minutes at low cost using a small portable easy-to-use, relatively inexpensive sample analysis device. In some uses, because of its small size and low cost, the sample analysis device can be reproduced in large numbers and distributed to many locations within one or more healthcare, residential, industrial, or commercial locations. In some applications, many units of the sample analysis device can be distributed and used in the field including at locations where equipment for sample analysis (for example, blood chemistry or CBC) is otherwise unavailable or prohibitively expensive.

We use the term "point-of-care" broadly to include, for example, any location in close physical proximity to a patient or other person to whom healthcare is being provided. In many cases, point-of-care refers to services provided in the physical presence of a patient, for example, in the same room or building or at the same place or within a short distance.

Although much of the discussion below refers to applications of the sample analysis technology to chemical analysis of whole blood drawn from a human or other animal, the sample analysis technology can also be applied to a wide range of contexts in which a sample (which may, but need not, be a biological sample) contains chemical components of interest (such as molecules or ions) and that may not involve counting and may or may not include particles, units, or other elements of one or more kinds that are to be counted.

We use the term "sample" broadly to include, for example, any fluid or other mass or body of material that contains one or more analyzable chemical components and may or may not also contain one or more countable units of one or more types. The countable units may in some cases be opaque, translucent, or otherwise non-transparent to incident light. The analyzable chemical components may in some instances be transparent, translucent, or otherwise non-opaque to incident light. In some examples, the sample is whole blood containing countable blood cells of different types and also containing analyzable chemical components such as molecules or ions, to name two.

We use the term "chemical components" broadly to include, for example, chemical compounds, ions, molecules, and other constituents of a sample that may not be present in a form of discernible (e.g., visible) countable units.

We use the term "unit of a chemical component" broadly to include, for example, a single unit of a chemical component such as a single molecule, ion, or other constituent. In typical samples, there are many units of a given type of chemical component, for example, many molecules of a chemical compound.

We use the term "countable units" broadly to include, for example, elements present in a sample that are discrete, discernible, visible, identifiable, and subject to enumeration. Typically, countable units are not transparent. In the case of whole blood, the countable units can include blood cells of different types.

We use the term "chemical analysis" broadly to include, for example, identification and quantification (e.g., determination of the level) of chemical components of one or more types in the sample. In some cases, chemical analysis can include identifying the presence of one or more molecules of one or more types and characterizing the amount, volume, or percentage of each of the types of molecules in the sample or in a particular volume of the sample.

As noted earlier, although the sample analysis technology has a broader range of applications, for convenience we sometimes discuss particular examples in which the sample includes whole blood or components of whole blood.

We use the term "whole blood" broadly to include, for example, blood in its original form drawn from a human or other animal. Whole blood includes countable units such as blood cells and blood plasma that includes chemical components. As described in the Wikipedia entry titled "Blood plasma" blood plasma is "a yellowish liquid component of blood that normally holds the blood cells in whole blood in suspension. In other words, it is the liquid part of the blood that carries cells and proteins. . . . It is mostly water (up to 95% by volume), and contains dissolved proteins (6-8%) (e.g. serum albumins, globulins, and fibrinogen), glucose, clotting factors, electrolytes ($Na^+$, $Ca^{2+}$, $Mg^{2+}$, $HCO_3^-$, $Cl^-$, etc.), hormones, carbon dioxide (plasma being the main medium for excretory product transportation) and oxygen." Clotting factors include molecules such as plasminogen and prothrombin that participate in clot formation.

We use the term "blood cells" broadly to include, for example, red blood cells (erythrocytes), white blood cells (leukocytes), rare blood cell types, ambiguous blood cell types, and platelets (thrombocytes).

As shown in FIG. 1, typical automated techniques 10 for chemical analysis of blood use fluorescence-based sandwich immunoassay techniques to identify and quantify acellular chemical components 12, for example, molecules of one or more chemical components in blood plasma 14. The "filling" of the "sandwich" in fluorescence-based sandwich immunoassay is, for example, molecules 16 of a given target chemical component in the blood plasma. Each of the molecules is, in effect, sandwiched 18 as a result of adding two types 20, 22 of antibodies to the blood sample. The antibodies of one type 20 are known to bind specifically to one location 24 on the target molecules and serve as "capture antibodies" in the sense that they provide a known "base" at which the target molecules are held. The antibodies of the other type 22 serve as "detection antibodies" and are also known to bind specifically to the target molecules, but to a different location 26 on the target molecules. In some examples, the capture antibodies are fixed, say, to a surface 28 and literally "capture" the target molecules and hold them at a particular location on the surface. The detection antibodies are typically marked by fluorescent molecules 30 attached to them.

Once the target molecules have been captured, that is, bound to the capture antibodies, high intensity excitation light 32 illuminates the sample in one wavelength band causing much lower intensity light to be emitted 34 from the attached fluorescent molecules in a different, typically longer, fluorescence wavelength band. The emitted light is sensed by a light detector 36 (after being passed through a filter 38 to block the much higher intensity excitation light). The light detector is highly sensitive to the presence and intensity level of the relatively low intensity fluorescence wavelength band light and can therefore generate signals indicating the fluorescence intensity and in turn the amount of the target chemical component present in the sample.

The fluorescence sandwich technique can be used to identify and quantify different target chemical components of blood simultaneously by using different appropriate pairs of capture antibodies and suitably labelled (by fluorescent molecules) detection antibodies. In some implementations of such multiplexing, the different capture antibodies are attached at different locations to a fixed surface as a way to differentiate the different target molecules based on their locations at the fixed surface. In some implementations, the target molecules remain dissolved or suspended in the sample and the different capture antibodies are marked using fluorescent beads (for example, Luminex® beads) that produce fluorescence light in different wavelength bands, or different combinations of the bands, as a way to differentiate the different types of target molecules without regard to their locations in the sample.

As discussed later, in some implementations of the sample analysis technology, chemical analysis is combined with a contact monolayer non-fluorescence imaging technique for performing a complete blood count (CBC). For several reasons, the standard fluorescence sandwich technique just described is not optimally compatible with the contact monolayer non-fluorescence CBC technique. One reason is that, in the contact CBC technique, the blood sample is typically in direct contact with a light-sensitive surface of an image sensor which precludes the inclusion of a filter element between the surface and the sample to block the high intensity excitation light. A second reason is that the contact CBC technique is not readily compatible with washing and other processing steps (one of which involves removing non-transparent blood cells from the sample) generally required in fluorescence sandwich immunoassay techniques. The washing and processing steps cannot be easily applied if the same whole blood sample used for the sample analysis technique is to be used also for the contact CBC technique. [Yet, as will be discussed later, because the contact CBC technique is based on the use of a monolayer of blood, portions of the monolayer are free of blood cells and contain only light-passing blood plasma. Therefore, although the entire area of the image sensor may not be suitable for chemical analysis of the target molecules because of the presence of blood cells, some portions of the area of the image sensor are suitable for the sample analysis technique even with whole blood.] A third reason why the fluorescent sandwich technique is not optimally compatible with the contact CBC technique described above is that the small size pixels of the high-resolution image sensor do not provide as adequate low-light sensitivity to detect the low intensity emitted fluorescence light as can a larger-area light detector.

The sample analysis technology that is described here can be used independently to perform chemical analysis of whole blood or can be used to perform chemical analysis of whole blood in combination with or to supplement (simultaneously or sequentially) a contact CBC technique that uses the same sample and light from the same light source. As a result, both the contact CBC technique and the blood chemical analysis can be performed quickly at essentially the same time on a tiny sample of whole blood (for example, a sample of less than 50 microliters or less then 15 microliters or less then 5 microliters) at the point-of-care using a small inexpensive device. Although we often discuss examples in which the chemical analysis is performed on whole blood, the sample analysis technology can be applied to raw whole blood or to whole blood that has been processed to alter or adjust or remove or supplement chemical components or to whole blood from which some or all of the blood cells have been removed, including blood plasma.

We use the term "contact CBC technique" broadly to include, for example, any technique in which blood cells of one or more types are identified and counted in a sample that is in contact with (e.g., within a near-field distance of) a surface of an image sensor. Additional information about contact CBC techniques can be found in one or more of United States patent publications 2016/0041200, 2014/0152801, 2018/0284416, 2017/0293133, 2016/0187235, and U.S. Pat. Nos. 9,041,790, 9,720,217, 10,114,203, 9,075, 225, 9,518,920, 9,989,750, 9,910,254, 9,952,417, 10,107, 997, all of which are incorporated here by reference.

Figure 2:
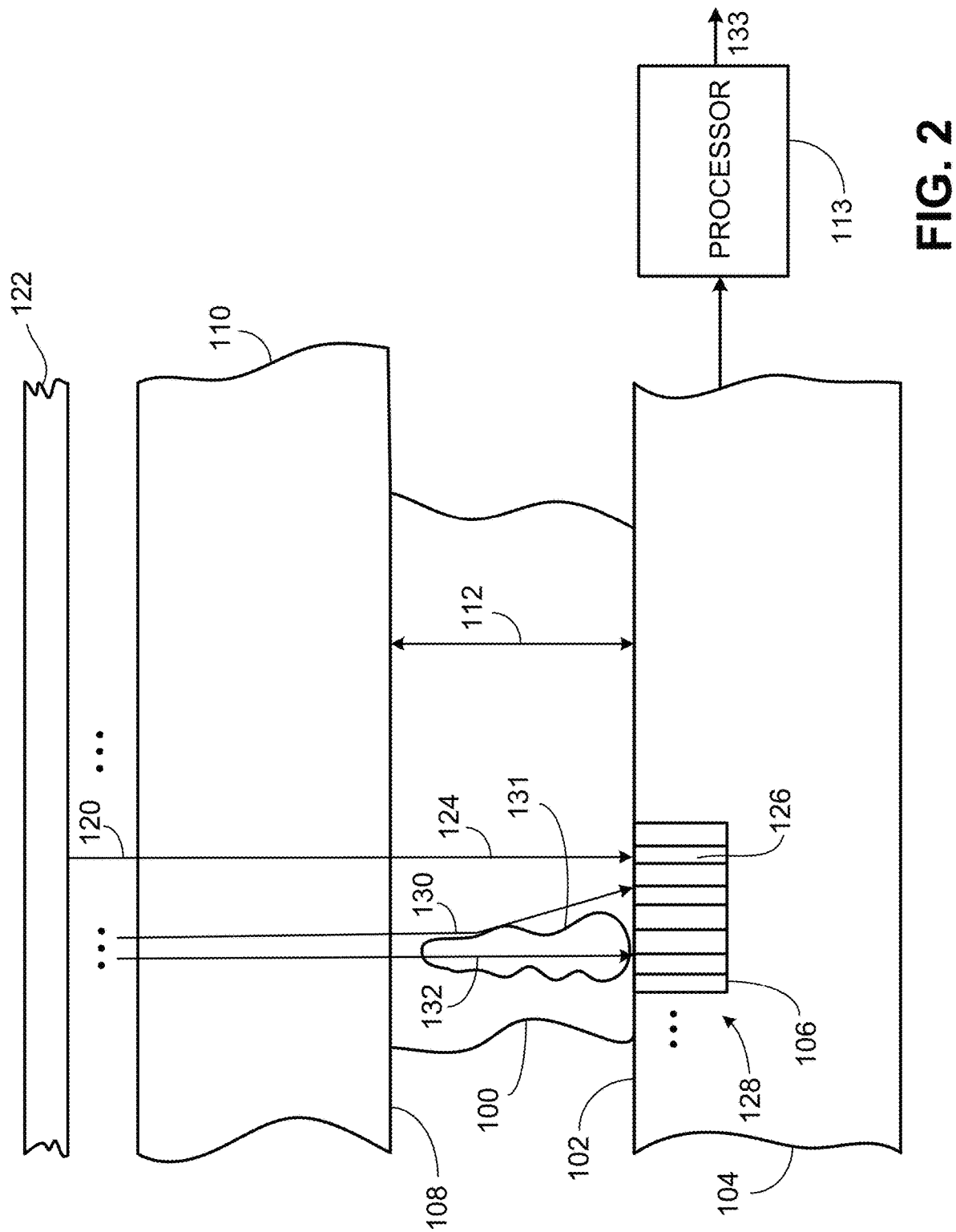
FIG. 2 is a schematic view of an example sample analysis device.

Referring to FIG. 2, in some implementations of the sample analysis technology, a monolayer 100 of whole blood is situated between a surface 102 of a high resolution image sensor 104 at which an array of photosensitive elements (e.g., pixels) 106 are exposed and a corresponding surface 108 of a lid 110, to form a monolayer having a known volume defined by its length, width, and thickness 112 between the surface 102 and the surface 108. Examples of structures and techniques for forming such a monolayer are described in one or more of United States patent publications 2016/0041200, 2014/0152801, 2018/0284416, 2017/0293133, 2016/0187235, and in U.S. Pat. Nos. 9,041,790, 9,720,217, 10,114,203, 9,075,225, 9,518,920, 9,989,750, 9,910,254, 9,952,417, 10,107,997, all of which are incorporated here by reference.

We use the term "high-resolution" broadly to include, for example, an image sensor that has a pixel spacing in one or both of two dimensions that is smaller than 5 µm, or 3 µm, or 1 µm, or sub-micron, for example.

We use the term "monolayer" broadly to include, for example, a volume of a sample that has a thickness no greater than the thickness of a particular type of unit in the sample, such as blood cells, so that across the monolayer two units cannot be stacked in the dimension defined by the thickness. In the case of a whole blood sample, the thickness of the monolayer could be in the range of 1 micrometer to 100 micrometers.

Light 120 from a light source 122 illuminates the monolayer 100. Portions 124 of the light may pass through the sample monolayer and be received by photosensitive elements 126 in the array 128 of the image sensor. Portions 130 of the light may be reflected or refracted by components 131 of the monolayer and the reflected or refracted light may be received by photosensitive elements in the array. Portions 132 of the light may be transmitted through components of the monolayer and the transmitted light may be received by photosensitive elements in the array; portions of the light may be absorbed by components of the monolayer. As discussed later, the components of the monolayer can include countable units, chemical components, beads, and other elements.

The light source can be configured or controlled or both to provide illuminating light in one or more selected wavelength bands and combinations of them. A wide variety of types of light sources and combinations of them can be used, for example, LEDs, LED panels, organic LEDs, fluorescent panels, incandescent lamps, ambient illumination, arrays of monochrome LEDs, arrays of narrowband sources such as red, green, and blue LEDs or lasers, a miniaturized color display such as a liquid crystal or organic LED (OLED) display or an RGB laser color projector.

Using the light that originates at the light source and passes through, is reflected or refracted by, or is transmitted through the monolayer, the image sensor captures one or more images of the monolayer including countable units of various types (for example, blood cells) and chemical components that are detectable (either in their native condition or as a result of being marked as discussed later). One or more of the captured images are processed by one or more processors or other image processing components 113 to produce information 133 about the whole blood sample including, for example, a CBC or a chemical analysis or both of the countable units and chemical components. Among other things, the resulting information can include a count of red blood cells and their hemoglobin content.

The CBC information can be generated by identifying and counting in the captured images the number of countable units of each type in the sample. Additional information about CBC techniques and about imaging using contact image sensors can be found, for example, in United States patent publications 2016/0041200, 2014/0152801, 2018/0284416, 2017/0293133, 2016/0187235, and in U.S. Pat. Nos. 9,041,790, 9,720,217, 10,114,203, 9,075,225, 9,518,920, 9,989,750, 9,910,254, 9,952,417, 10,107,997, all of which are incorporated here by reference.

Figure 3:
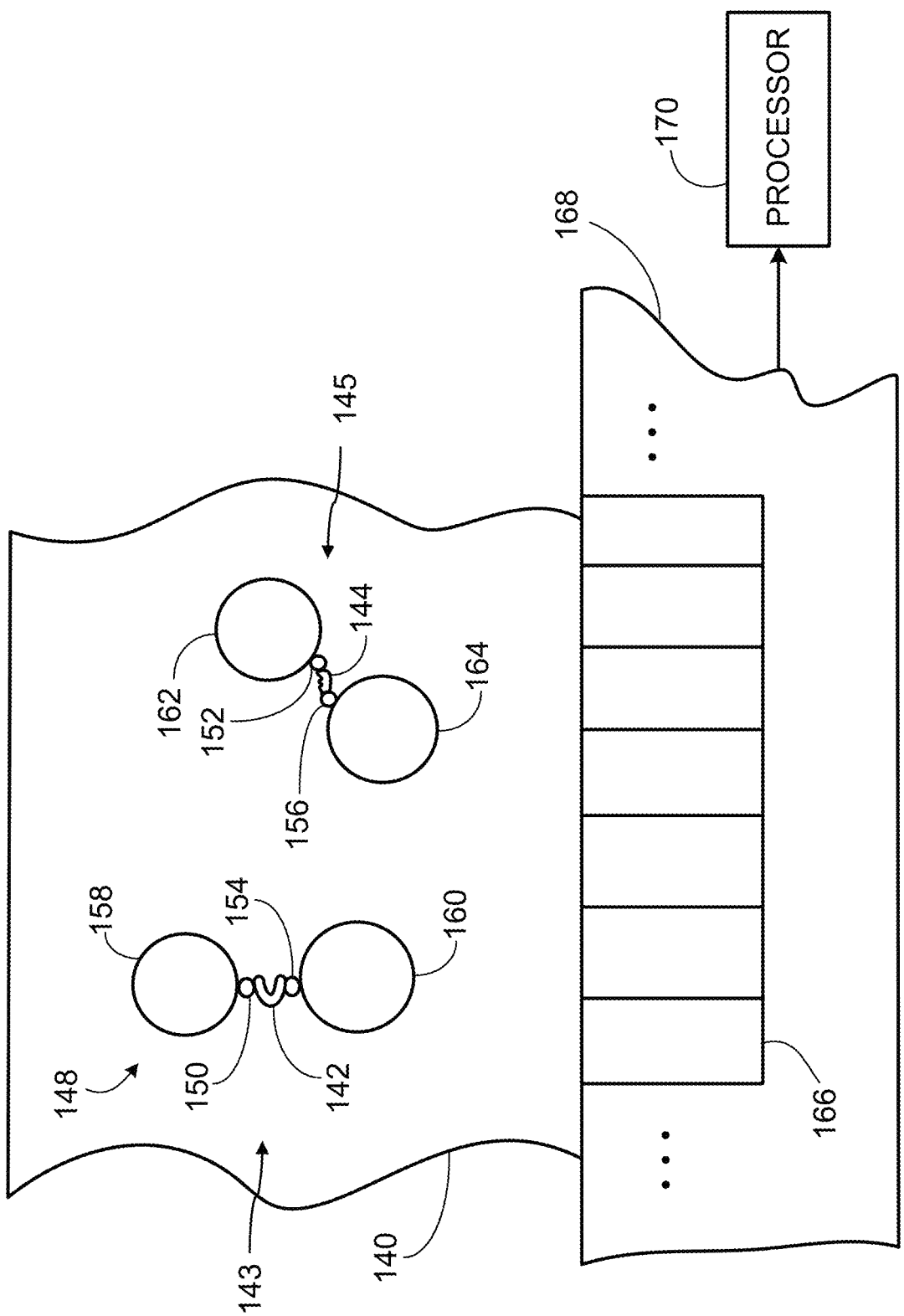
FIG. 3 is a schematic view of an example bead-complexing technique for sample analysis.

As shown in FIG. 3, a monolayer 140 of whole blood (such as the same monolayer of whole blood used for the contact CBC technique) can be used for chemical analysis of various chemical components 142, 144 of the whole blood. For this purpose, individual units of the different types of chemical components of the whole blood monolayer sample can be treated as fillings of sandwiches 148 similar to the fluorescent sandwiches. However, in implementations of the sample analysis technology described here, capture antibodies 150, 152 and detection antibodies 154, 156 are attached to beads 158, 160, 162, 164 that need not have fluorescent properties and are directly visible or otherwise detectable using light that originates at the light source and passes through, is reflected or refracted by, or is transmitted through the monolayer or components of the monolayer. The resulting light is received by light-sensitive elements (e.g., pixel) 166 arrayed in the image sensor 168. (Unlike fluorescence techniques, the light source is not within the monolayer sample but is external to it.)

Using the received light (in some cases, the same received light used for the contact CBC technique), the image sensor captures one or more images of the monolayer sample. One or more processors 170 or other image processing devices process the one or more received images and apply a variety of techniques to identify the presence of and determine the level (e.g., quantity, amount, volume, percentage) of each of the chemical components in the sample.

The beads 158, 160, 160, 162 to which the antibodies 150, 152 and 154, 156 are attached need not have fluorescent properties. The beads can have characteristics that are detectable, visible, or otherwise discernible based on light from the light source that is reflected from, refracted by, or passes through them. We sometimes refer to such beads as "direct indicator beads". The direct indicator beads can take the form of what are sometimes call microbeads in reference to their small size. Microbeads have sizes typically in the range of 0.5 to 500 micrometers.

We use the term "direct indicator beads" (or sometimes simply "beads") broadly to include, for example, any tag, marker, or other indicator device or indicator characteristic that can be attached to or associated with a chemical component of a sample and is identifiable at a sensor using received light that was incident on and reflected or refracted by or transmitted through the indicator device or characteristic. In some cases, direct indicator beads can take the form of small grains, particles, beads, spherules, or other elements, and combinations of them, and can be of a variety of shapes, sizes, materials, and colors.

To determine the presence of units of chemical components in the sample, the processor analyzes the images to detect directly discernible characteristics of beads and complexes of two or more beads that are revealed by light originating from the light source and reflected from, refracted by, or transmitted through the beads to the surface of the image sensor.

We use the term "directly discernible characteristics" of beads and complexes of beads broadly to include, for example, any quality, attribute, or other trait that can be detected, determined, or derived from light that originated at a light source and was reflected from, refracted by, or transmitted through the beads. Directly discernible characteristics could include color, size, texture, birefringence, or shape, or combinations of them, for example.

We use the term "complexes of beads" broadly to include, for example, two or more beads that can be associated with one another because they are attached to a unit in a sample, such as a molecule or other chemical component. Typically, the two or more beads of a complex are detectable in constant close proximity (e.g., touching) one to another. In some cases, the two or more beads of a complex are detectable because they have two or more predetermined different directly discernible characteristics. For example, two beads of a complex may have two specific different colors that are discernible by processing the images from the image sensor.

We use the word "attach" to include both direct and indirect attachment. For example, two particles, units, or other elements may be attached directly (e.g., in contact and bound) to one another, or indirectly (e.g., attached to one another by an attachment unit bound to each of the two particles, units, or other elements).

We use the term "attachment unit" broadly to include, for example, any antibodies (e.g., an antibody directed against a cluster-of-differentiation cell surface antigen if the target unit is a specific cell type), capsid proteins or other antigens from a pathogenic virus (e.g., if the target unit is an antibody to the pathogenic virus, indicating prior exposure to the pathogenic virus), and other binding molecules and structures suitable for binding or attachment (e.g., direct attachment) to a unit of a chemical component.

The sample analysis technology that we describe here can be applied in a variety of different modes.

In some examples of one such mode, which we sometimes call the complexed-beads mode, the chemical components remain dissolved or suspended in the sample. A capture antibody and a detection antibody, each coupled to a separate direct indicator bead, bind simultaneously to the two different locations on a given target molecule or other unit of a target chemical component to form a complex of two beads (i.e., a doublet). [Because each direct indicator bead has more than one of its particular (capture or detection) antibody bound to its surface, a bead may participate in more than one such complex simultaneously, forming a triplet or higher-order bead complex.]

By processing one or more images captured by the image sensor, it is possible to identify those beads present in doublets or higher-order complexes, and thus associated with the chemical component. By determining the proportion of complexed beads to the total number of beads (complexed and singleton, that is, uncomplexed) identified in the sample, it is possible to determine the level or amount or quantity or concentration of the target units (e.g., molecules) of the chemical component in the sample.

It is true that identified singleton beads are not necessarily beads unbound to the target molecule, because in some cases only the capture antibody or the detection antibody, but not both, may have bound to the target molecule.

However, under constant incubation conditions and provided that the concentrations of bead-coupled capture antibodies and bead-coupled detection antibodies in the sample are constant and their ratio is known, it is possible empirically to establish a "standard curve" that represents the relationship between the bead complex index (that is, the proportion of complexed beads to total beads identified by the device) and the concentration of the target molecule.

Figure 4:
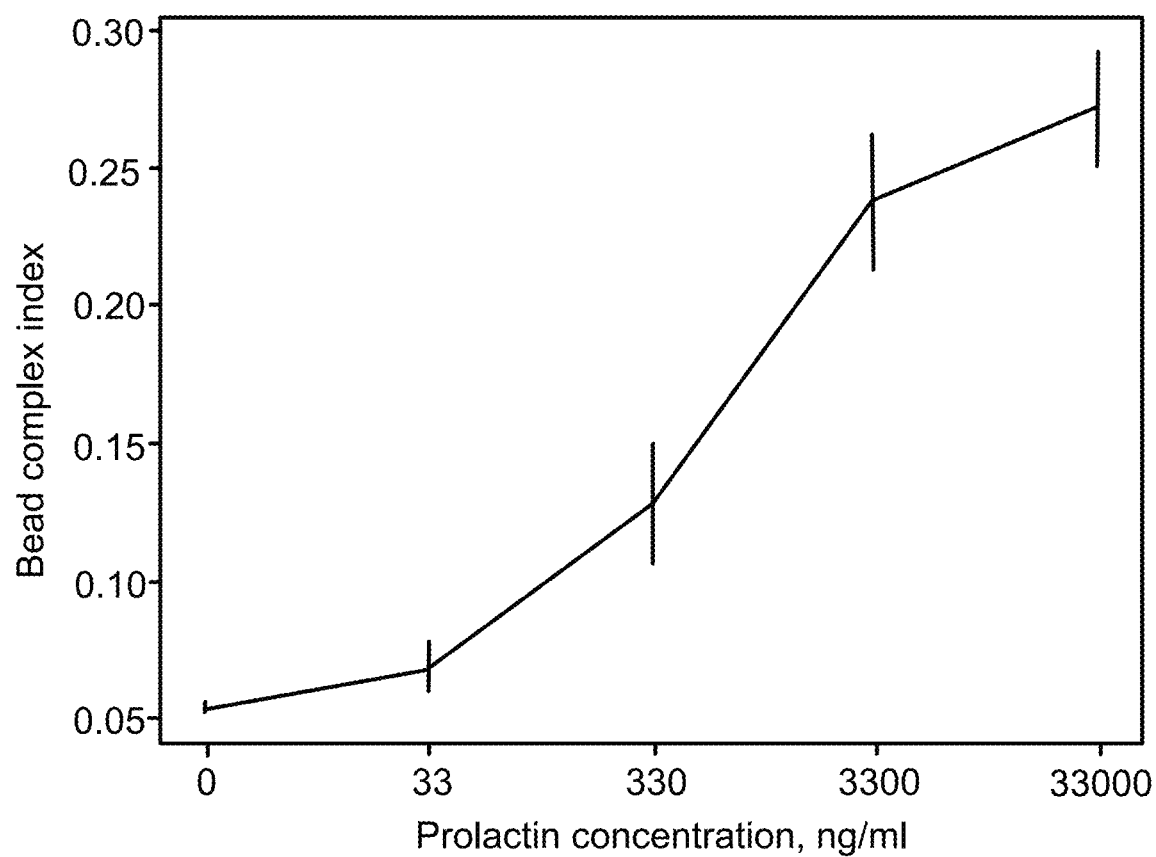
FIG. 4 is a graph of a standard curve.

This has been done experimentally for prolactin to generate the standard curve shown in FIG. 4. Using the standard curve, it is possible to determine the otherwise unknown concentration of prolactin in a sample by determining the bead complex index under identical incubation conditions.

In some implementations, the same beads can be used to mark both the capture antibodies and the detection antibodies that will bind to given units of the chemical component. In some implementations, by using complexes of beads having different directly discernible characteristics for capture antibodies and detection antibodies that are to be attached to the units of different chemical components it is possible to multiplex the process of detecting the presence and levels of the different chemical components at the same time. Multiplexing can be achieved by using beads having different colors, sizes, shapes, textures, or other directly discernible characteristics.

Figure 5:
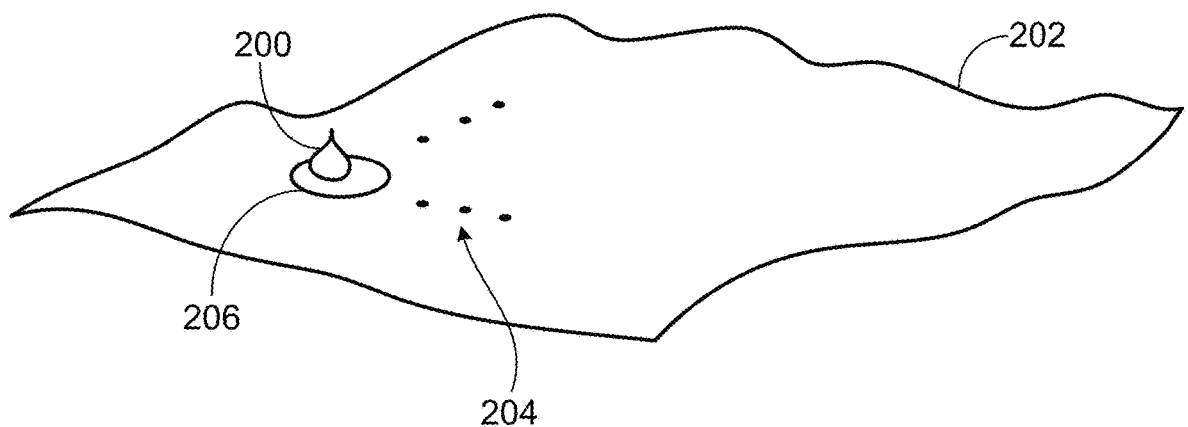
FIG. 5 is a schematic view of an example surface including capture antibodies.

As shown in FIG. 5, in some implementations, the capture antibodies 200 are irreversibly bound to a fixed surface 202, for example different types of capture antibodies are bound as spots 206 in known corresponding locations in an array 204 on the fixed surface. In such implementations the capture antibodies need not have direct indicator beads attached to them, but the detection antibodies would have direct indicator beads attached to them. The fixed surface could be the surface 108 of the lid 110 that faces the surface 102 of the image sensor 104 and defines a gap occupied by the monolayer 100 of the sample. When the monolayer of the sample is in the gap and in contact with the printed spots in the array of capture antibodies, respective chemical components in the sample will bind to respective capture antibodies, based on the type of the chemical components, in positions defined by the locations of the printed spots in the array, and can at the same time bind to detection antibodies coupled to direct indicator beads. Images captured using incident light that passes through the monolayer and is reflected, refracted or transmitted by the direct indicator beads can then be processed to identify and determine the amounts of different types of chemical components based on the imaged locations of the beads attached to the detection antibodies. This technique of chemical analysis can be used separately or in combination with the contact CBC technique discussed earlier.

In some implementations, a combination of the location-based chemical analysis technique and the in-solution or in-suspension (that is, non-location-based, complexed-beads mode) chemical analysis technique could be used.

In order to use these chemical analysis techniques in combination with the CBC technique in a point-of-care setting, steps must be taken to impart the bead-coupled antibodies to the sample before it is loaded onto the image sensor surface. One approach would be to pass the sample of blood taken from the patient through a tube where dried bead-coupled antibodies are solubilized by the blood and allowed to bind with the target molecules. Then the prepared sample can be placed on the sensor surface. Another approach would be to deposit the bead-coupled antibodies onto the surface 108 of the lid 110 (in some cases in addition to bead-free capture antibodies irreversibly bound at specific locations of the lid) so that they are solubilized when the lid encounters the blood sample in forming the monolayer.

In some implementations, the target unit of the chemical component includes at least one of an antigen, a hormone, a biomarker, a drug, a viral capsid, a pathogen-directed antibody (for example, a virus-directed antibody), an oligonucleotide, or another molecule, cell, or particle.

In some implementations, a bead is bound to an attachment unit, and the attachment unit is bound to the target unit of the chemical component. In the example of FIG. 3, attachment units 150 and 154 are bound to a first target unit 142 of a first chemical component, and attachment units 152 and 156 are bound to a second target unit 144 of a second chemical component. Beads 158 and 160 are bound to attachment units 150 and 154, respectively, to form a multi-bead complex 143 that includes beads 158 and 160, attachment units 150 and 154, and target unit 142. Beads 162 and 164 are bound to attachment units 152 and 156, respectively, to form a multi-bead complex 145 that includes beads 162 and 164, attachment units 152 and 156, and target unit 144. In some implementations, it is the proximity of the beads 162 and 164 to one another or the constancy of the proximity or both that allows for the identification of the multi-bead complex. The proximity can be measured in terms of absolute distance, or proportion of the dimension of one or more of the beads, for example.

The attachment units 150, 152, 154, 156 can be, but need not be, detection antibodies or capture antibodies. In addition to, or alternatively to, antibodies, the attachment units 150, 152, 154, 156 may include a capsid protein or other antigen of a pathogenic virus. The attachment units 150, 154 may be different from one another.

The target units 142 and 144 of the chemical component may include at least one of an antigen, a hormone, a biomarker, a drug, a viral capsid, a pathogen-directed antibody (for example, a virus-directed antibody), an oligonucleotide, or another molecule, cell, or particle. The attachment units 150, 152 (for example) may include proteins of a virus, the proteins binding to an antibody 142 of the virus.

In some implementations, the beads 158, 160 are different from one another in one or more characteristics such as size, color, shape, surface properties, translucency, weight, and combinations of them.

Figure 6:
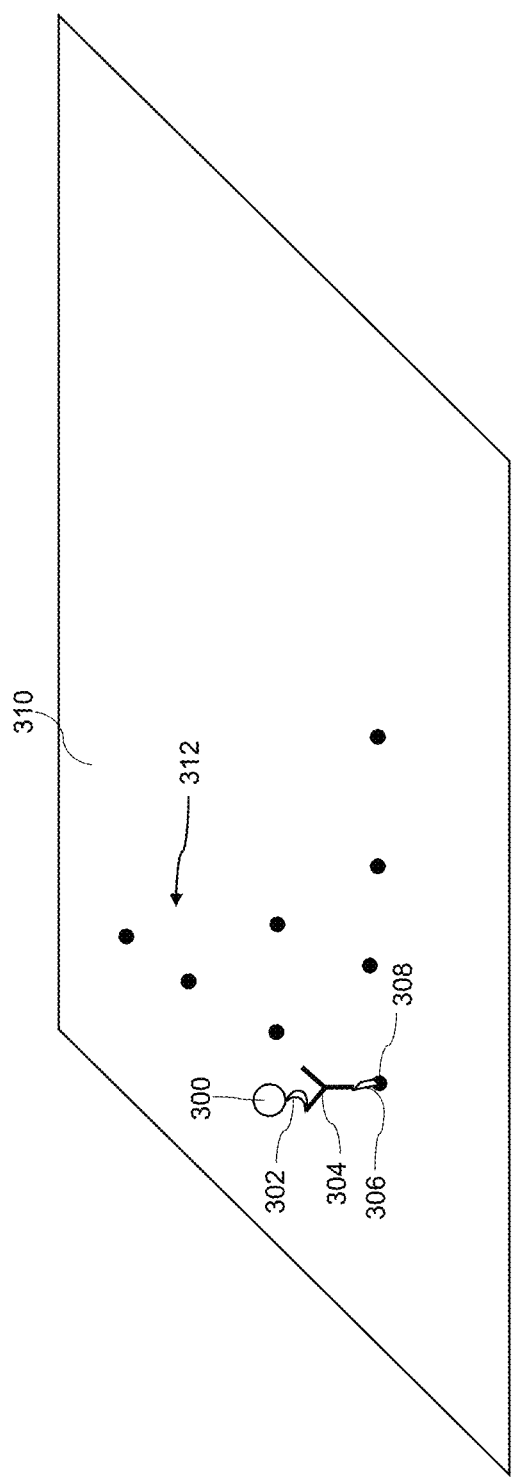
FIG. 6 is a schematic view of an example surface including a bound attachment element.

As shown in FIG. 6, in some implementations, an attachment unit 306 (for example, a capture unit, capture particle, or other capture element) is bound at a known location 308 on a surface 310 (e.g., a surface of an image sensor, or a surface of a lid). The surface 310 may include an array of known locations 312, each known location corresponding to a known type of attachment unit (not shown, except for 306). The attachment unit 306 is bound to a target unit 304 of a chemical component, which is bound to an attachment unit 302. The attachment unit 302 is bound to a direct indicator bead 300. As described in reference to FIG. 5, because the attachment unit 306 is of a known type (e.g., a type known to bind to the target unit 304 of the chemical component) and in a known location, imaging of the direct indicator bead 300 and determination of the known location 308 may be used to determine an amount or presence or both of the chemical component.

The attachment units 302 and 306 can be, but need not be, antibodies, and can include types of attachment units as described above in reference to FIG. 3. The target unit 304 of the chemical component may include at least one of an antigen, a hormone, a biomarker, a drug, a viral capsid, a pathogen-directed antibody (for example, a virus-directed antibody), an oligonucleotide, or another molecule, cell, or particle.

In some implementations, a capture bead includes an attachment unit. In some implementations, a surface (for example, the surface 310) includes an attachment unit.

Various choices of the target units and attachment units may be used in a variety of applications, such as cytometry, in vitro diagnostics, environmental analysis, multiplex biochemical assays, serology, and gene expression and combinations of them.

In an example of serology applied to a sample of blood from a patient, beads are bound to recombinant viral proteins of an infectious virus. The recombinant viral proteins bind to antibodies of the infectious virus within the sample. Complexes of two or more of the beads associated with an antibody of the infectious virus are identified or enumerated or both, and results of the identification or enumeration or both (potentially in concert with the identification or enumeration or both of single un-complexed beads) are used to determine a presence or level or both of the antibody of the infectious virus, as described earlier. Based on the determined presence or level or both of the antibody of the infectious virus, past exposure by the patient to the infectious virus can be identified. Samples besides blood may be used in addition to or instead of blood.

Other implementations are also within the scope of the following claims.

The invention claimed is:

1. An apparatus comprising:
an image sensor having
an array of light sensitive elements at a sensor surface, and
a first surface; and
one or more processors configured to:
cause the image sensor to capture one or more images of a sample disposed on the first surface, wherein the sample comprises a unit of a chemical component, the unit of the chemical component bound to a first attachment unit and a second attachment unit,
wherein the first attachment unit is attached to a bead, and
wherein the second attachment unit is
attached at a location on the first surface, or
attached at a location on a second surface, wherein, when the second attachment unit is attached at the location on the second surface, the second surface comprises an upper surface with respect to the first surface of the apparatus, the upper surface facing the first surface,
such that the bead is attached to the first surface or the second surface through the unit of the chemical component, and
wherein the array of light sensitive elements is disposed and structured to capture the one or more images based on light originating at a light source, reflected by, refracted by, or transmitted through the bead, and received at the array of light sensitive elements at the sensor surface, and wherein the array of light sensitive elements has a pixel spacing that is smaller than 5 μm,
receive, from the image sensor, data representative of the captured one or more images of the sample disposed on the first surface,
identify the bead in at least one image of the one or more images of the sample,
identify, in the at least one image of the one or more images of the sample, the location at which the second attachment unit is attached on the first surface or on the second surface based on the identification of the bead, and
bound to the chemical component which is bound to the first attachment unit attached to the bead, a presence or a level of the chemical component in the sample.

2. The apparatus of claim 1, wherein the second attachment unit is attached to the first surface, and wherein the first surface comprises the sensor surface.

3. The apparatus of claim 1, comprising the second surface,
wherein the second surface is a surface of a lid that defines a gap occupied by the sample, and wherein the second attachment unit is attached to the second surface.

4. The apparatus of claim 3, wherein the second surface is arranged to form a layer of the sample with a thickness in a range from 1 µm to 100 µm between the second surface and the sensor surface.

5. The apparatus of claim 1, wherein the first attachment unit and the second attachment unit comprise antibodies.

6. The apparatus of claim 1, wherein the first attachment unit and the second attachment unit comprise antigens from a pathogen, and wherein the unit of the chemical component comprises an antibody to the pathogen.

7. The apparatus of claim 6, wherein the pathogen comprises a virus.

8. The apparatus of claim 1, wherein the second attachment unit is printed on the first surface or the second surface.

9. The apparatus of claim 1, wherein a plurality of attachment units, including the second attachment unit, are attached at respective locations on the first surface or the second surface, the respective locations forming an array.

10. The apparatus of claim 1, wherein the sample comprises whole blood of a human or animal.

11. An apparatus comprising:
an image sensor having
an array of light sensitive elements at a sensor surface, and
a surface; and
one or more processors communicatively coupled to the image sensor, configured to:
cause the image sensor to use the array of light sensitive elements to capture one or more images of a sample disposed on the surface, wherein the sample comprises a plurality of multi-bead complexes, each multi-bead complex of the plurality of multi-bead complexes comprising two or more respective beads attached to a respective unit of a chemical component, and
wherein the array of light sensitive elements is disposed and structured to capture one or more images based on light originating at a light source and reflected by, refracted by, or transmitted through the two or more respective beads of each multi-bead complex and received at the array of light sensitive elements at the sensor surface, and wherein the array of light sensitive elements has a pixel spacing that is smaller than 5 µm,
receive, from the image sensor, data representative of the captured one or more images of the sample disposed on the surface,
measure, in at least one image of the one or more images of the sample, a proximity to one another of the two or more respective beads of at least two different multi-bead complexes of the plurality of multi-bead complexes, and
identify, in the at least one image, two or more separate multi-bead complexes based on the measured proximity to one another of the two or more respective beads of the at least two different multi-bead complexes.

12. The apparatus of claim 11, wherein the one or more processors are configured to identify a presence or a level of the chemical component in the sample, based on the identification of the two or more separate multi-bead complexes.

13. The apparatus of claim 11, wherein the one or more processors are configured to enumerate a number of the plurality of multi-bead complexes in the sample.

14. The apparatus of claim 11, wherein the sample comprises attachment units, and wherein, for each multi-bead complex comprising two or more respective beads attached to the respective unit of the chemical component,
two or more respective attachment units are bound to the respective unit of the chemical component, and
each attachment unit of the two or more respective attachment units is bound to at least one bead of the two or more respective beads,
such that each multi-bead complex of the plurality of multi-bead complexes comprises the two or more respective beads, the two or more respective attachment units, and the respective unit of the chemical component.

15. The apparatus of claim 14, wherein the two or more respective attachment units of each multi-bead complex of the plurality of multi-bead complexes comprise antibodies.

16. The apparatus of claim 14, wherein the two or more respective attachment units of each multi-bead complex of the plurality of multi-bead complexes comprise antigens from a pathogen, and
wherein the respective unit of the chemical component of each multi-bead complex of the plurality of multi-bead complexes comprises an antibody to the pathogen.

17. The apparatus of claim 16, wherein the pathogen comprises a virus.

18. The apparatus of claim 14, wherein at least two attachment units of the two or more respective attachment units of each multi-bead complex of the plurality of multi-bead complexes are different from one another.

19. The apparatus of claim 14, wherein the two or more respective attachment units of each multi-bead complex of the plurality of multi-bead complexes are configured to bind at different locations at the respective unit of the chemical component of the multi-bead complex.

20. The apparatus of claim 11, wherein at least two beads of the two or more respective beads of a first multi-bead complex of the plurality of multi-bead complexes differ in at least one of appearance, reflective characteristics, refractive characteristics, or transmissive characteristics, for the light originating at the light source.

* * * * *